United States Patent
Commons et al.

[11] Patent Number: 5,190,940
[45] Date of Patent: Mar. 2, 1993

[54] CHOLESTEROL ESTER HYDROLASE INHIBITORS

[75] Inventors: Thomas J. Commons, Wayne; Richard E. Mewshaw, Norristown; Donald P. Strike, St. Davids, all of Pa.

[73] Assignee: American Home Products Corporation, New York, N.Y.

[21] Appl. No.: 796,500

[22] Filed: Nov. 22, 1991

Related U.S. Application Data

[62] Division of Ser. No. 582,687, Sep. 14, 1990, Pat. No. 5,112,859.

[51] Int. Cl.$^5$ .................. A61K 31/54; A61K 31/535; A61K 31/445; A61K 31/495
[52] U.S. Cl. .................. 514/227.5; 514/237.5; 514/255; 514/330; 544/58.4; 544/172; 544/389; 546/221
[58] Field of Search .................. 544/58.4, 172, 389; 546/221; 514/227.5, 237.5, 255, 330

[56] References Cited

U.S. PATENT DOCUMENTS
3,275,512 9/1966 Lemin .................. 514/490

OTHER PUBLICATIONS
Bhat et al., Biochem. Biophys. Res. Commun. 109(2) 486 (1982).
Hosie et al., J. Biol. Chem., 262(1) 260 (1987).
Stout et al., Biochim. Biophys. Acta, 837 6 (1985).
Scofield et al., Biochemistry, 16, (11) 2492 (1977).
Ogawa et al., Chem., Pharm. Bull., 34 (3) 1118 (1986).
Lombardo, Biochim. Biophys. Acta, 700 75 (1982).
Gallo et al., Proc. of the Soc. for Exper. Biol. and Med., 156 277 (1977).
Gallo et al., J. Lipid Res., 25 604 (1984).
Chem. Abstract 19492 (Abstract of Belg. 654, 121).
Sonnet et al., J. Econ. Entomology, 64 (6) (1971) 1378.

*Primary Examiner*—Mukund J. Shah
*Assistant Examiner*—Matthew V. Grumbling
*Attorney, Agent, or Firm*—Richard K. Jackson

[57] ABSTRACT

The compounds of the formula:

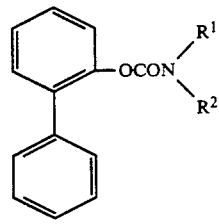

in which $R^1$ is hydrogen or alkyl; $R^2$ is alkyl, cycloalkyl, cycloalkylalkyl, phenylalkyl or alkylphenylalkyl; or $R^1$ and $R^2$ taken together complete a heterocyclic moiety of the formula:

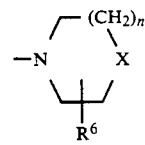

in which X is

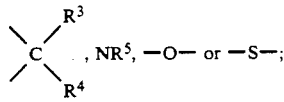

, $NR^5$, $-O-$ or $-S-$;

where $R^3$, $R^4$ and $R^5$ are, independently hydrogen, alkyl, phenyl or substituted phenyl, in which the substituents are halogeno, alkoxy or trifluoromethyl; $R^6$ is hydrogen, alkyl or gemdialkyl and n is one of the integers 0, 1 or 2, are cholesterol ester hydrolase inhibitors useful in the treatment of high serum cholesterol levels and associated disease states in the mammal such as coronary heart disease, atherosclerosis, familial hypercholesterolemia, hyperlipemia, and the like.

6 Claims, No Drawings

CHOLESTEROL ESTER HYDROLASE INHIBITORS

This is division of application Ser. No. 07/582,687 filed Sep. 14, 1990 now U.S. Pat. No. 5,112,859.

BACKGROUND OF THE INVENTION

Full absorption of dietary cholesterol into the bloodstream is dependent upon cholesterol esterase (cholesterol ester hydrolase; CEH) activity [Bhat et al., Biochem. Biophys. Res. Commun. 109 486 (1982); Gallo et al., J. Lipid Research 25 604 (1984)]. The removal of cholesterol esterase from pancreatic juice results in an eighty percent reduction in absorbed cholesterol. By inhibiting the action of cholesterol esterase, serum cholesterol levels can be beneficially controlled.

Hosie et al., J. Biological Chem. 262 260 (1987) discusses the irreversible inhibition of cholesterol esterase by p-nitrophenyl N-alkyl carbamates and the reversible inhibition of cholesterol esterase by cholesterol-N-alkyl carbamates.

DESCRIPTION OF THE INVENTION

In accordance with this invention, there is provided a group of compounds which inhibit cholesterol absorption of the formula:

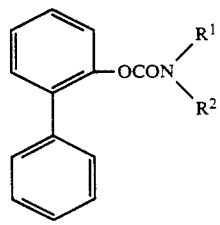

in which
  $R^1$ is hydrogen or alkyl of 5 to 20 carbon atoms;
  $R^2$ is alkyl of 5 to 20 carbon atoms, cycloalkyl of 5 to 8 carbon atoms, cycloalkylalkyl of 6 to 10 carbon atoms, phenylalkyl of 7 to 11 carbon atoms or alkylphenylalkyl of 8 to 17 carbon atoms; or
  $R^1$ and $R^2$ taken together with the nitrogen atom to which they are attached complete a heterocyclic moiety of the formula:

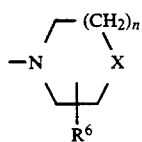

in which
  X is

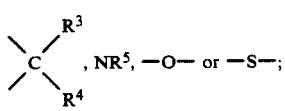

where
  $R^3$, $R^4$ and $R^5$ are, independently, hydrogen, alkyl of 1 to 6 carbon atoms, phenyl or substituted phenyl in which the substituent is alkyl of 1 to 6 carbon atoms, halogeno, alkoxy of 1 to 6 carbon atoms or trifluoromethyl;
  $R^6$ is hydrogen, alkyl of 1 to 6 carbon atoms or gemdialkyl of 2 to 12 carbon atoms; and
  n is one of the integers 0, 1 or 2.

The preferred compounds from the standpoint of their potency are those of the formula:

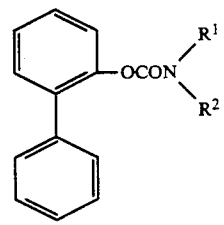

in which
  $R^1$ is hydrogen;
  $R^2$ is cycloalkyl of 5 to 8 carbon atoms and most preferably 6 carbon atoms, cycloalkylalkyl of 6 to 10 carbon atoms and most preferably 7 carbon atoms; or phenylalkyl of 7 to 11 carbon atoms and most preferably 10 carbon atoms; and
  $R^1$ and $R^2$ taken together with the nitrogen atom to which they are attached are:

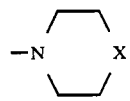

in which
  X is

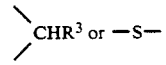

where $R^3$ is -H or phenyl.

The compounds of this invention are prepared from 2-phenylphenol by reaction with $R^2NCO$ in the presence of a base such as triethylamine, or by conversion of 2-phenylphenol to its chloroformate with

followed by reaction with the desired amine $HNR^1R^2$ under conventional conditions.

The following examples illustrate without limitation the preparation of representative compounds of the invention:

EXAMPLE 1

Octylcarbamic acid[1.1'-biphenyl]-2-yl ester

Triethylamine (3.3 mL, 23.7 mmol) is added dropwise under a nitrogen atmosphere to a solution of 2-phenylphenol (5.0 g, 29.3 mmol) and octyl isocyanate (5.5 g, 35.5 mmol) in 75 mL of methylene chloride. After the addition, the solution is stirred overnight at room temperature. The solution is washed with 1N HCl, dried (MgSO4) and the solvent removed under reduced pressure to give 10.09 g of a tan solid. Recrystallization from diisopropyl ether-hexane gives the title compound as a white crystalline solid (6.88 g, 72%), mp 59°-60° C.

Elemental analysis for $C_{21}H_{27}NO_2$: Calc'd: C, 77.50; H, 8.36; N, 4.30; Found: C, 77.51; H, 8.58; N, 4.52.

EXAMPLE 2

[[4-(2,2-Dimethylpropyl)phenyl]methyl]heptylcarbamic acid[1,1'-biphenyl]-2-yl ester Trichloromethyl chloroformate (2.1 mL, 17.4 mmol) is added dropwise over ten minutes under a nitrogen atmosphere to a solution of 2-phenylphenol (3.0 g, 17.6 mmol) in 50 mL of methylene chloride at ice bath temperature. After the addition of trichloromethyl chloroformate, triethylamine (2.5 mL, 17.9 mmol) is added dropwise over a ten minute period and the reaction mixture is stirred at ice bath temperature for 2.5 hours. A solution of N-[[4-(2,2-dimethylpropyl)phenyl]methyl]heptylamine (4.8 g, 17.4 mmol) and triethylamine (2.5 mL, 17.9 mmol) in methylene chloride (15 mL) is added at ice bath temperature over a thirty minute period. Then the ice bath is removed and the reaction mixture is stirred overnight. The reaction mixture is washed with 1N HCl, 5% NaHCO$_3$, dried over MgSO$_4$ and the solvent removed in vacuo to give, after purification by high pressure liquid chromatography (hexane-methylene chloride) the title compound as a light brown oil (2.37 g, 29% of theory), MS/me, 471 (M+).

Elemental analysis for $C_{32}H_{41}NO_2$: Calc'd: C, 81.48; H, 8.76; N, 2.97; Found: C, 81.15; H, 8.92; N, 2.92.

EXAMPLE 3

Cyclohexylcarbamic acid[1,1'-biphenyl]-2-yl ester

In the same manner as described in Example 1, the title compound is produced as a white crystalline solid after recrystallization of the crude reaction product from diisopropyl ether (3.68 g, 42%), mp 119°-121° C.

Elemental analysis for $C_{19}H_{21}NO_2$: Calc'd: C, 77.26; H, 7.17; N, 4.74; Found: C, 77.26; H, 7.24; N, 4.81.

EXAMPLE 4

(Cyclohexylmethyl)carbamic acid[1,1'-biphenyl]-2-yl ester

In the same manner as described in Example 2, the title compound is produced as a white crystalline solid (1.16 g, 13%) after purification of the crude reaction product by HPLC (hexane-ethyl acetate), mp 107°-109° C.

Elemental analysis for $C_{20}H_{23}NO_2$: Calc'd: C, 77.64; H, 7.49; N, 4.53; Found: C, 77.75; H, 7.48; N, 4.62.

EXAMPLE 5

(4-Phenylbutyl)carbamic acid[1,1'-biphenyl]-2-yl ester

In the same manner as described in Example 2, the title compound is produced as a light yellow oil (1.85 g, 18%) after purification of the crude reaction product by HPLC (hexane-ethyl acetate), MS m/e, 345 (M+).

Elemental analysis for $C_{23}H_{23}NO_2$: Calc'd: C, 79.97; H, 6.71; N, 4.05; Found: C, 79.84; H, 6.81; N, 4.08.

EXAMPLE 6

3,3-Dimethyl-1-piperidinecarboxylic acid[1,1'-biphenyl]-2-yl ester

In the same manner as described in Example 2, the title compound is produced as a light yellow oil (3.36 g, 37%) after purification of the crude reaction product by HPLC (hexane-methylene chloride), MS m/e, 309 (M+).

Elemental analysis for $C_{20}H_{23}NO_2$: Calc'd: C, 77.64; H, 7.49; N, 4.53; Found: C, 77.27; H, 7.63; N, 4.50.

EXAMPLE 7

1-Piperidinecarboxylic acid[1,1'-biphenyl]-2-yl ester

In the same manner as described in Example 2, the title compound is produced as a yellow oil (2.70 g, 33%) after purification of the crude reaction product by HPLC (hexane-methylene chloride), MS m/e, 281 (M+).

Elemental analysis for $C_{18}H_{19}NO_2$: Calc'd: C, 76.84; H, 6.81; N, 4.98; Found: C, 76.83; H, 6.81; N, 4.92.

EXAMPLE 8

4-Methyl-1-piperidinecarboxylic acid[1,1'-biphenyl]-2-yl ester

Trichloromethyl chloroformate (3.54 mL, 29.4 mmol) is added dropwise under a nitrogen atmosphere to a solution of 2-phenylphenol (10.0 g, 58.8 mmol) in 150 mL of benzene at room temperature. After the addition, dimethylaniline (7.45 mL, 58.8 mmol) is added dropwise at such a rate that the temperature of the reaction mixture is maintained between 20°-25° C. The resulting mixture is stirred at room temperature for 3 hours. A solution of 4-methylpiperidine (6.95 mL, 58.8 mmol) and dimethylaniline (7.45 mL, 58.8 mmol) in 50 mL of benzene is then added dropwise. After the addition the reaction is stirred at room temperature overnight. The reaction mixture is washed with 1N HCl, 5% NaHCO$_3$, dried (MgSO$_4$) and the solvent removed under reduced pressure. Purification of the crude reaction product by HPLC (hexane-methylene chloride) followed by recrystallization from diisopropyl ether gives the title compound as a white crystalline solid (10.8 g, 62), mp 85°-86° C.

Elemental analysis for $C_{19}H_{21}NO_2$; Calc'd: C,77.26; H, 7.17; N, 4.74; Found: C, 77.43; H, 7.10; N, 4.82.

EXAMPLE 9

4-Phenyl-1-piperidinecarboxylic acid[1.1'-biphenyl]-2-yl ester

In the same manner as described in Example 8, the title compound is produced as a white crystalline solid (13.4 g, 64%) after purification by HPLC (hexane-methylene chloride), mp 76°-78° C.

Elemental analysis for $C_{24}H_{23}NO_2$: Calc'd: C, 80.64; H, 6.48; N, 3.92; Found: C, 80.69; H, 6.57; N, 3.94.

EXAMPLE 10

4-Morpholinecarboxylic acid[1.1'-biphenyl]-2-yl ester

In the same manner as described in Example 8, the title compound is produced as a white crystalline solid (11.8 g, 71%) after purification by HPLC (hexane-ethyl acetate), mp 87°-88° C.

Elemental analysis for $C_{17}H_{17}NO_3$: Calc'd: C, 72.07; H, 6.05; N, 4.94; Found: C, 71.95; H, 6.02; N, 4.88.

EXAMPLE 11

4-Thiomorpholinecarboxylic acid[1.1'-biphenyl]-2-yl ester

In the same manner as described in Example 8, the title compound is produced as a crystalline solid (12.1 g, 69%) after purification by HPLC (hexane-methylene chloride), mp 112°-114° C.

Elemental analysis for $C_{17}H_{17}NO_2S$: Calc'd: C, 68.20; H, 5.72; N, 4.69; Found: C, 68.39; H, 5.64; N, 4.63.

EXAMPLE 12

4-Methyl-1-piperazinecarboxylic acid[1,1'-biphenyl]-2-yl ester

The same general method used in Example 8 is followed. At the end of the reaction the mixture is extracted with 1N HCl. The organic layer is separated. The aqueous layer is partitioned with ethyl acetate, made basis with 5% NaHCO$_3$, and extracted. The organic layer is separated, dried (MgSO$_4$) and the solvent removed under reduced pressure to give a liquid containing crystals. The crystals are collected by filtration. Recrystallization of this material from diisopropyl ether gives the title compound as a white crystalline solid, mp 79°–81° C.

Elemental analysis for $C_{18}H_{20}N_2O_2$: Calc'd: C, 72.95; H, 6.80; N, 9.45; Found: C, 73.03; H, 6.72; N, 9.43.

EXAMPLE 13

4-Phenyl-1-piperazinecarboxylic acid[1,1'-biphenyl]-2-yl ester

In the same manner as described in Example 8, the title compound is produced as a white crystalline solid after crystallization of the crude reaction mixture from ethyl acetate and recrystallization of the material isolated from diisopropyl ether, mp 117°–119° C.

Elemental analysis for $C_{23}H_{22}N_2O_2$: Calc'd: C, 77.07; H, 6.19; N, 7.82; Found: C, 76.83; H, 6.29; N, 7.81.

The compounds of this invention are inhibitors of cholesterol ester hydrolase. It has been shown that removal of the enzyme from pancreatic juice results in an 80% reduction in the uptake of cholesterol into the bloodstream in rats [J. Biol. Chem. 262, 260 (1987)]. The association between high serum cholesterol levels and coronary heart disease is well documented; consequently, compounds which inhibit CEH are useful for treating atherosclerosis, familial hypercholesterolemia, hyperlipemia, and like diseases.

The ability of the compounds of this invention to inhibit the formation of cholesteryl esters and thereby interfere with and prevent assimilation of cholesterol into the lymphatic system and ultimately the blood stream was established by incubating the compounds at 37° C. with a mixture of cholesterol and oleic acid in the presence of buffered cholesterol esterase [(EC 3.2.2.13) Sigma No. C-1892, from bovine pancreas] and measuring the amount of ester formed, according to the procedure of Field, J. of Lipid Research, 25 389 (1984). The concentration of test compound that inhibits one-half of the ester formation (IC$_{50}$, μM) is given in the following Table.

The in vivo cholesterol absorption studies were conducted in normal rats by oral administration of the compound being tested suspended in olive oil followed by oral administration of [4-$^{14}$C] cholesterol in propylene glycol, otherwise following the procedure of Cayen et al., J. Lipid Res. 20 162 (1979). The serum radioactivity was measured at six hours after dosing. The results of this study are reported in the following Table, where available, as percent decrease compared to control.

| Compound of Example | In Vitro Results IC$_{50}$ (μM) Against CEH | In Vivo Results Effects on Absorption of $^{14}$C-Chol.-6 hr-Normal Rat |
|---|---|---|
| 1 | 1.5 | |
| 2 | 100 | |
| 3 | 5 | 21% decrease at 100 mg/kg |
| 4 | 3 | 21% decrease at 100 mg/kg |
| 5 | 0.25 | 46% decrease at 250 mg/kg |
| 6 | 38 | |
| 7 | 0.08 | 19% decrease at 250 mg/kg |
| 8 | 0.8 | |
| 9 | 1.9 | 11% decrease at 100 mg/kg |
| 10 | 26 | |
| 11 | 1.2 | 21% decrease at 100 mg/kg |
| 12 | 25 | |
| 13 | 53 | |

Thus, the compounds of this invention are useful in the treatment of high serum cholesterol levels and associated disease states such as coronary heart disease, atherosclerosis, familial hypercholesterolemia, hyperlipemia and similar disease states. As such, they may be administered to a hypercholesterolemic patient, orally or parenterally, in an amount sufficient to reduce serum cholesterol concentrations to the desired level. The dosage regimen for therapeutic use of the anti-hypercholesterolemic agents of this invention will vary with the route of administration, size and age of the person under treatment, as well as the severity of the dysfunction under treatment. Therefore, the treatment must be individualized for the patient under guidance of the attending physician.

The compounds of this invention may be administered by conventional oral or parenteral routes as solids, liquids or isotonic solutions. Conventional adjuvants known to the art may be combined with the compounds to provide compositions and solutions for administration purposes, although it is considered desirable and feasible to use the compounds neat or pure without additives other than for the purpose of providing suitable pharmaceutically acceptable solid or liquid dosage units.

What is claimed is:

1. A compound of the formula:

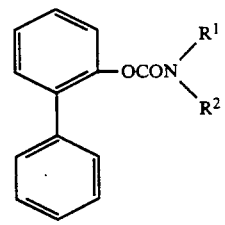

in which
R$^1$ and R$^2$ taken together with the nitrogen atom to which they are attached complete a heterocyclic moiety of the formula:

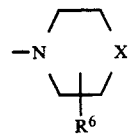

in which

X is $NR^5$, —O— or —S—;

where $R^5$ is hydrogen, alkyl of 1 to 6 carbon atoms, phenyl or substituted phenyl in which the substituent is alkyl of 1 to 6 carbon atoms, halogeno, alkoxy of 1 to 6 carbon atoms or trifluoromethyl; and $R^6$ is hydrogen, alkyl of 1 to 6 carbon atoms or gem-dialkyl of 2 to 12 carbon atoms.

2. The compound of claim 1 which is 4-morpholinecarboxylic acid[1,1'-biphenyl]-2-yl ester.

3. The compound of claim 1 which is 4-thiomorpholinecarboxylic acid[1,1'-biphenyl]-2-yl ester.

4. The compound of claim 1 which is 4-methyl-1-piperazinecarboxylic acid[1,1'-biphenyl]-2-yl ester.

5. The compound of claim 1 which is 4-phenyl-1-piperazinecarboxylic acid[1,1-biphenyl]-2-yl ester.

6. A process for reducing chloesterol absorption in a mammal in need of reduced serum cholesterol levels which comprises administering orally or parenterally, an amount of a compound of the following formula sufficient to reduce plasma cholesterol concentration:

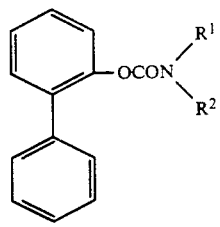

in which
$R^1$ is hydrogen;
$R^2$ is cycloalkyl of 5 to 8 carbon atoms and most preferably 6 carbon atoms, cycloalkylalkyl of 6 to 10 carbon atoms and most preferably 7 carbon atoms; or phenylalkyl of 7 to 11 carbon atoms and most preferably 10 carbon atoms;

and
$R^1$ and $R^2$ taken together with the nitrogen atom, to which they are attached are:

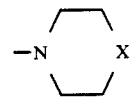

in which
X is

or —S— where $R^3$ is -H or phenyl.

* * * * *